United States Patent [19]

Berdahl et al.

[11] Patent Number: 4,808,731

[45] Date of Patent: Feb. 28, 1989

[54] METHOD FOR MAKING OXYDIPHTHALIC ANHYDRIDE

[75] Inventors: Donald R. Berdahl, Scotia; Pamela A. Matsch, Schenectady, both of N.Y.

[73] Assignee: General Electric Company, Schenectady, N.Y.

[21] Appl. No.: 164,283

[22] Filed: Mar. 4, 1988

[51] Int. Cl.$^4$ .............................................. C07D 307/89
[52] U.S. Cl. ................................................... 549/241
[58] Field of Search ......................................... 549/241

[56] References Cited

U.S. PATENT DOCUMENTS

| | | | |
|---|---|---|---|
| 4,513,141 | 4/1985 | Brunelle et al. | 548/476 |
| 4,697,023 | 9/1987 | Schwartz et al. | 549/241 |

FOREIGN PATENT DOCUMENTS

| | | |
|---|---|---|
| 80122738 | 9/1980 | Japan . |
| 80136246 | 10/1980 | Japan . |
| 046916 | 3/1985 | Japan . |

OTHER PUBLICATIONS

Markezich, R. L. & Zamek, O.S., "Reactions of Fluoride and Nitrite Ions with 4-Nitrophthalimides", J. of Organic Chemistry, vol. 42 (1977) pp. 3431-3434.

Primary Examiner—Richard L. Raymond
Attorney, Agent, or Firm—William A. Teoli; James C. Davis, Jr.; James Magee, Jr.

[57] ABSTRACT

Oxydiphthalic anhydride is prepared by effecting contact between a substituted phthalic anhydride such as 4-nitro or 4-fluoro phthalic anhydride and a dialkylaminopyridine in the presence of a refluxing nonpolar organic solvent.

8 Claims, No Drawings

METHOD FOR MAKING OXYDIPHTHALIC ANHYDRIDE

BACKGROUND OF THE INVENTION

The present invention relates to a method for making oxydiphthalic anhydride involving contact between nitrophthalic anhydride and a catalytic amount of a dialkylaminopyridine in the presence of a nonpolar organic solvent under reflux conditions.

Oxydiphthalic anhydride, and moreparticularly 4,4'-oxydiphthalic anhydride, is a well-known monomer useful in the synthesis of polyimides having good thermal properties and high solvent resistance. Oxydiphthalic anhydride or "ODAN" has been prepared by heating 4-nitrophthalic anhydride with a sodium or potassium nitrite in a dipolar aprotic solvent, as shown by Japanese Patent Document No. 80/136,246 (Chem. Abstracts 95:42680 (1981). Another procedure for making ODAN is shown by Schwartz et al., U.S. Pat. No. 4,697,023, incorporated herein by reference, employing a halophthalic anhydride, water, and an alkali metal compound such as potassium fluoride or potassium carbonate in the presence of a dipolar aprotic solvent. An additional procedure for making ODAN is based on the hydrolysis of the corresponding 4,4'-oxybis(N-methylphthalimide) which can be made by the procedure of Markezich et al. "Reactions of Fluoride and Nitride Ions With 4-Nitrophthalimide", Journal of Organic Chemistry 42, 3431 (1977), or as shown in copending application Ser. No. 881,415, filed July 2, 1986, now U.S. Pat. No. 4,780,544.

Although the above-described procedures can be used to make ODAN, employment of a dipolar aprotic solvent, such as dimethylsulfoxide, is economically unattractive while the hydrolysis procedure from the corresponding bisimide requires an additional processing step.

A further procedure for making certain aromatic ethers is shown by Brunelle et al., U.S. Pat. No. 4,513,141, by effecting the displacement of reactive radicals on an activated aromatic nucleus using a dialkylamino branched alkyl-substituted pyridinium salt as a phase transfer catalyst. Although improved yields of bis(aromatic ethers) are achieved, a phase transfer catalyst must be used which is not commercially available, and which requires several steps to make.

The present invention is based on the discovery that ODAN, and preferably 4,4'-oxydiphthalic anhydride, can be made by heating 4-nitrophthalic or 4-fluorophthalic anhydride in the presence of dialkylaminopyridine and a nonpolar solvent such as dichlorobenzene. Unexpectedly, the reaction can be done in a nonpolar solvent, in the absence of an added phase transfer catalyst.

STATEMENT OF THE INVENTION

There is provided by the present invention, a method for making oxydiphthalic anhydride having the formula,

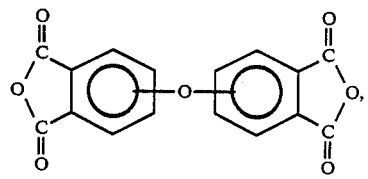

Which comprises,
(1) agitating a mixture comprising a substituted phthalic anhydride of the formula,

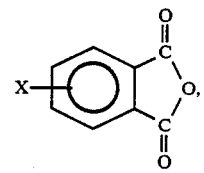

a nonpolar organic solvent, and an effective amount of a dialkylaminopyridine having the formula,

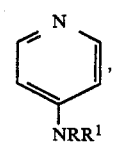

at a temperature in the range of from 150° C. to 250° C. to produce a mixture comprising oxydiphthalic anhydride,
(2) purifying the oxydiphthalic anhydride in the mixture of (1) by
  (a) converting the oxydiphthalic anhydride to the corresponding tetra acid salt in situ, recovering the tetra acid salt, converting the salt to the tetra acid and dehydrating it to oxydiphthalic anhydride, or
  (b) separating the solids from the mixture of (1), and
    (i) recovering substantially pure oxydiphthalic anhydride by recrystallization from an organic solvent or by sublimation, or
    (ii) converting the recovered solids to substantially pure oxydiphthalic anhydride as shown in (a), where R and $R^1$ are members selected from the same or different $C_{(1-8)}$ alkyl radicals, and x is selected from nitro or fluoro.

Substituted phthalic anhydride which can be used in the practice of the method of the present invention are compounds such as, 3-nitrophthalic anhydride and 4-nitrophthalic anhydride, 3-fluorophthalic and 4-fluorophthalic anhydride.

Dialkylaminopyridines which are included within formula (3) are, for example, N,N-dimethylaminopyridine, 4-pyrrolinopyridine, 4-piperidinopyridine, 4-morpholinopyridine, and 4-(4-methyl-1-piperidino)pyridine.

An effective amount of dialkylaminopyridine is from about 5 mole % to 100 mole % of dialkylaminopyridine, based on the total moles of substituted phthalic anhydride.

Suitable nonpolar organic solvents which can be used in the practice of the method of the present invention are, for example, o-dichlorobenzene and 1,2,4-trichlorobenzene.

Dehydrating agents which can be used to convert the oxybis(phthalic diacid) to the corresponding oxybis(phthalic anhydride) are acetic anhydride, acetic anhydride/acetic acid mixtures. Thermal dehydration in a solvent such as o-DCB also can be used.

Solvents which can be used to recrystallize ODAN are, for example, acetic acid, cyclohexanone, and anisolee.

Sublimation temperatures which can be used are 175° C. to 210° C. at 0.001 to 0.5 torr.

In order that those skilled in the art will be better able to practice the present invention, the following examples are given by way of illustration and not by way of limitation. All parts are by weight.

EXAMPLE 1

A mixture of 9.66 grams (50 millimole) of 4-nitrophthalic anhydride, 0.61 gram (5 millimole) of 4-dimethylaminopyridine, and 18 mL (30% solid) of o-dichlorobenzene was heated at reflux for 22 hours. The mixture was then analyzed with HPLC using aliquots which were treated with acetonitrile and IN HCL. There was shown a complete disappearance of the starting nitro anhydride. The reaction mixture was cooled and a black, somewhat sticky solid was removed by filtration. The black solid was treated with 20 mL of 50% aqueous sodium hydroxide and 50 mL of water. It was then heated until dissolved. The resulting solution was then filtered through glass microfiber filter paper and added dropwise to a heated concentrated aqueous solution of HCL. The resulting suspension was then continuously extracted with diethylether over a 12-hour period. Evaporation of the ether provided 6.22 grams or 72% of a tannish-yellow solid having a melting point of 220°-224° C. with decomposition. Based on method of preparation, and its melting point, the product was 4,4'-oxydiphthalic acid. The oxydiphthalic acid was converted to the corresponding oxydianhydride by recrystallization in a mixture of 12 mL of acetic anhydride and 25 mL of acetic acid. There was obtained 3.2 grams (57%) of product having a melting point of 224°-226.5° C. Based on method of preparation, the product was 4,4'-oxydiphthalic anhydride.

EXAMPLE 2

The procedure of Example 1 was repeated except that in place of the reflux condenser, there was used a calcium hydride filled trap and condenser system. A mixture of 9.7 grams (50 mL) of 4-nitrophthalic anhydride, 4-(4-methylpiperidino)pyridine (0.88 grams, 5 mmol) and 12.7 mL of HPLC grade o-dichlorobenzene, sufficient to provide a mixture of 39% solids, was refluxed for 6 hours. There was obtained a 51% yield of 4,4'-oxydiphthalic anhydride as shown by HPLC using PIC reagents after 6 hours.

A similar reaction was run except that 4-ethylpyridine was used. The reaction was run at 39% solids in 12 ml of o-dichlorobenzene. After 18 hours, HPLC showed only 11% of 4,4'-oxydiphthalic acid. These results showed the superior performance of dialkyl aminopyridine of formula (3), such as dimethylaminopyridine of Example (1) or 4-(4-methylpiperidino)pyridine.

EXAMPLE 3

A mixture of 4-fluorophthalic anhydride (4.08 g, 24.6 millimole), 4-dimethylaminopyridine (0.305 g, 2.5 millimole) and o-dichlorobenzene (7.6 mL, solution=39% solids) was heated at reflux for 12 hours. Aliquots which were removed periodically and treated with acetonitrile, water and phosphoric acid and analyzed by HPLC using ion suppression techniques under reversed phase conditions showed the formation of 4,4-oxydianhydride. In treating the aliquots in this manner, anhydride groups are hydrolyzed to diacids (4,4-oxydianhydride is analyzed as oxydiphthalic acid, for example). After 12 hours, the very dark reaction mixture was cooled to room temperature, and filtered. The solid was rinsed several times with toluene and dried on the filter giving a crude yield of 2.27 g. The solid was treated with 2N NaOH (18 mL) and the resulting suspension was heated to boiling, filtered, cooled and added to a heated flask containing rapidly stirring, concentrated HCl at reflux (24 mL). The resulting suspension was extracted with diethyl ether in a continuous manner for 16 hours. Evaporation of the ether extract gave oxydiphthalic acid as a light tan solid: 1.50 g, 35%, mp 217°-221° C. with decomposition. HPLC analysis of isolated solid shows it to be contaminated with approximately 3-4% 4-fluorophthalic acid.

Although the above examples are directed to only a few of the very man variables which can be used in the practice of the method of the present invention, it should be understood that the present invention is directed to the use of a much broader variety of reactants and reagents as shown in the description proceeding these examples.

What is claimed and sought to be protected by Letters Patent of the United States is as follows:

1. A method for making oxydiphthalic anhydride having the formula,

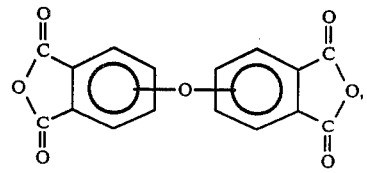

which consists of:
(1) agitating a mixture comprising a substituted phthalic anhydride of the formula,

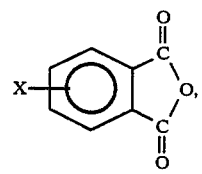

a nonpolar organic solvent, and an effective amount of a dialkylaminopyridine having the formula,

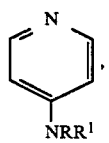

at a temperature in the range of from 150° C. to 250° C. to produce a mixture comprising oxydiphthalic anhydride, and
(2) recovering the oxydiphthalic anhydride from the mixture of (1), where R and R¹ are members selected from the same or different $C_{(1-8)}$ alkyl radicals, and X is a member selected from the class consisting of nitro and fluoro.

2. A method in accordance with claim 1, where the dialkylaminopyridine is 4-dimethylaminopyridine.

3. A method in accordance with claim 1, where the nonpolar organic solvent is o-dichlorobenzene.

4. A method in accordance with claim 1, where the oxydiphthalic anhydride is recovered by recrystallization.

5. A method in accordance with claim 1, where the oxydiphthalic anhydride is recovered by sublimitation.

6. A method in accordance with claim 1, where the oxydiphthalic anhydride is recovered by converting the oxydiphthalic anhydride to the tetra acid salt followed by conversion to the tetra acid and dehydration.

7. A method in accordance with claim1, where the substituted phthalic anhydride is 4-nitrophthalic anyhydride.

8. A method in accordance with claim 1, where the substituted phthalic anhydride is 4-fluorophthalic anhydride.

* * * * *